(12) United States Patent
Shimamura et al.

(10) Patent No.: US 7,692,710 B2
(45) Date of Patent: Apr. 6, 2010

(54) SOLID-STATE IMAGING DEVICE AND ELECTRONIC ENDOSCOPE USING THE SAME

(75) Inventors: Hitoshi Shimamura, Kurokawa-gun (JP); Kazuaki Takahashi, Saitama (JP); Kazuhiro Nishida, Minami-Ashigara (JP)

(73) Assignees: FUJIFILM Corporation, Tokyo (JP); Fujinon Corporation, Saitama-shi, Saitama (JP)

( * ) Notice: Subject to any disclaimer, the term of this patent is extended or adjusted under 35 U.S.C. 154(b) by 458 days.

(21) Appl. No.: 11/702,221

(22) Filed: Feb. 5, 2007

(65) Prior Publication Data
US 2007/0182843 A1    Aug. 9, 2007

(30) Foreign Application Priority Data
Feb. 3, 2006    (JP) .............................. 2006-027705

(51) Int. Cl.
*H04N 5/225*    (2006.01)
(52) U.S. Cl. .............................. 348/340; 348/45; 348/65
(58) Field of Classification Search ................... 348/45, 348/67, 76, 86–87, 294–301, 340–341, 373, 348/65, 72; 600/100, 110, 169, 101, 109, 600/117–120
See application file for complete search history.

(56) References Cited

U.S. PATENT DOCUMENTS

| 4,918,521 A | * | 4/1990 | Yabe et al. ..................... 348/76 |
| 5,376,960 A | * | 12/1994 | Wurster ........................ 348/76 |
| 6,416,463 B1 | * | 7/2002 | Tsuzuki et al. .............. 600/130 |
| 7,126,637 B2 | * | 10/2006 | Nakamura et al. .......... 348/340 |
| 2006/0164510 A1 | * | 7/2006 | Adler ........................... 348/65 |

FOREIGN PATENT DOCUMENTS

JP    5-15489 A    1/1993

OTHER PUBLICATIONS

Chinese Office Action dated Jul. 10, 2009.

* cited by examiner

*Primary Examiner*—Tuan Ho
*Assistant Examiner*—Don Nguyen
(74) *Attorney, Agent, or Firm*—Sughrue Mion, PLLC (57) ABSTRACT

A solid-state imaging device comprises: a solid-state imaging element comprising a solid-state imaging element body; a first substrate one end face of which is bonded to and integrated with one end face of a solid-state imaging element substrate of the solid-state imaging element, the first substrate comprising on its one surface an electrode for establishing electrical contact with a bonding wire led from a pad provided on one surface of the solid-state imaging element, a frame that seals the solid-state imaging element so as to surround outer peripheral surfaces of the solid-state imaging element substrate excluding its the one end face; and a sealing resin portion that covers a region extending from a portion including the electrode on the one surface of the first substrate to a portion including the pad on the one surface of the solid-state imaging element.

12 Claims, 11 Drawing Sheets

PRIOR ART

SOLID-STATE IMAGING DEVICE AND ELECTRONIC ENDOSCOPE USING THE SAME

BACKGROUND OF THE INVENTION

1. Field of the Invention

The present invention relates to a solid-state imaging device and an electronic endoscope using the same, and more particularly to a solid-state imaging device of such as a chip size package (CSP) type having microlenses integrated on a chip as well as an electronic endoscope having the solid-state imaging device.

2. Description of the Related Art

Various electronic type endoscope apparatuses have been proposed and developed for biomedical use so as to be inserted into body cavities and effect such as the observation of their interiors. In addition, various solid-state imaging elements including charge coupled devices (CCDs) are used in these electronic type endoscope apparatuses.

Figure 9:
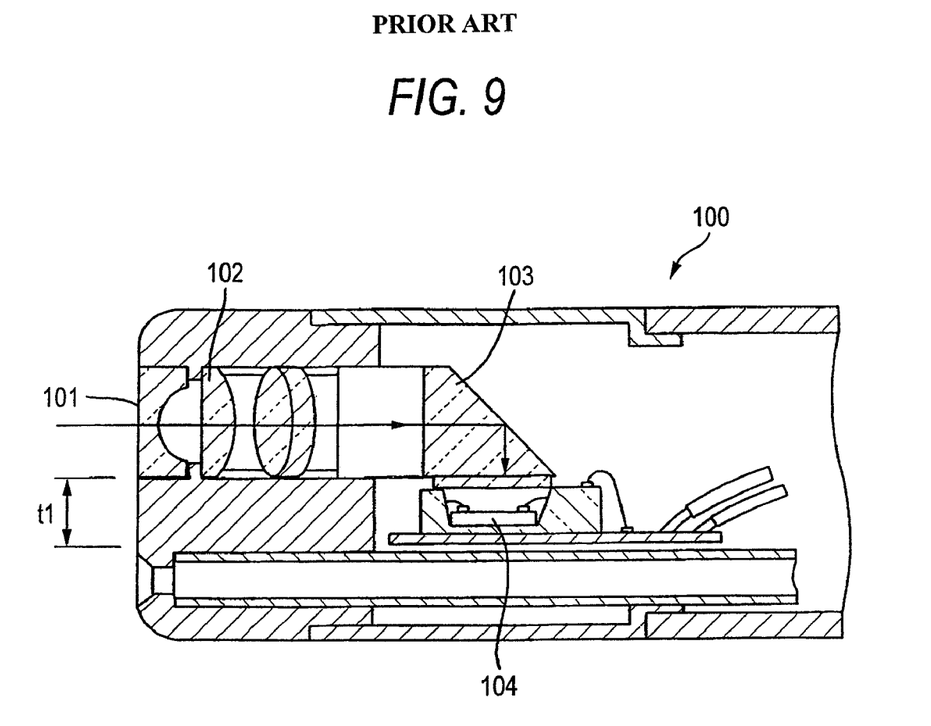
FIG. 9 is a cross-sectional view of essential portions illustrating a distal end portion of an electronic endoscope with the related-art solid-state imaging device installed therein.
Figure 10:
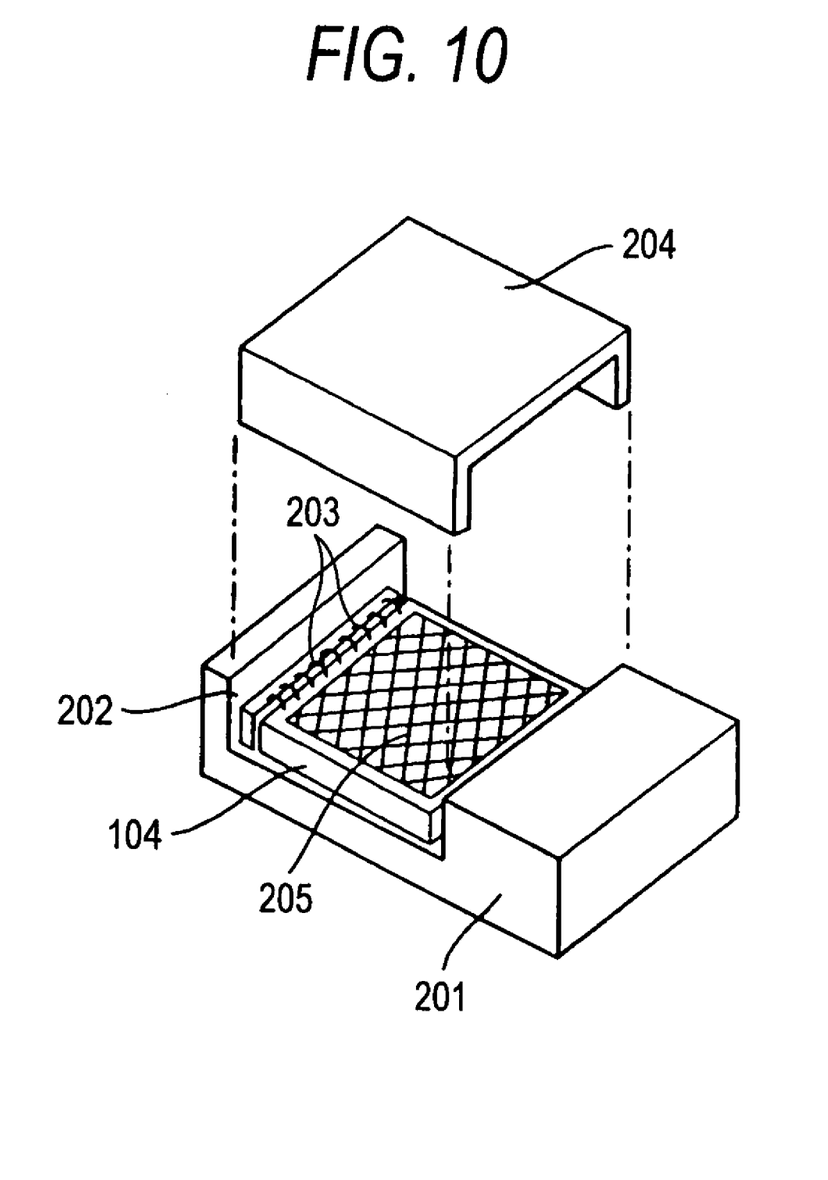
FIG. 10 is an exploded perspective view illustrating the related-art solid-state imaging device.

In the case of a direct viewing type, for instance, an electronic type endoscope apparatus is known which is constructed such that, as shown in FIG. 9, a solid-state imaging element 104 is installed in the interior of a distal end portion of an endoscope 100 in which an objective lens 102 facing an observation window 101 at a distal end face, as well as a prism 103 and the like adjacent thereto, are provided (e.g., refer to JP-A-5-15489). In addition, as shown in FIG. 10, this solid-state imaging element 104 is accommodated in an accommodating groove 202 of a package body 201, and is electrically connected to the package body 201 side and further to the endoscope body side by means of a bonding wire 203. It should be noted that in the drawing reference numeral 204 denotes a cover glass, and 205 denotes a color filter.

As for solid-state imaging elements used in such electronic type endoscopes and the like, there have been demands for compact-sized, thin-shaped, and moisture-resistant solid-state imaging elements. In addition, particularly in a case where the solid-state imaging element is used for such as biomedical use, because it is necessary to insert the endoscope into a narrow organ and the like inside the body, there has been an increasing demand for smaller-diameter endoscope bodies. Under these circumstances, the solid-state imaging elements are also required to be further compact and thinner in size, and the overall size of a solid-state imaging device including the package body of the solid-state imaging element is also required to be substantially the same size as the solid-state imaging element. Additionally, the solid-state imaging device is also required to be moisture resistant. For example, in the case of the solid-state imaging device shown in FIG. 9, since the solid-state imaging element 104 is mounted in the package body 201, the thickness of the overall solid-state imaging device is substantially large at t1.

SUMMARY OF THE INVENTION

The invention has been devised in view of the above-described circumstances, and has as an object to provide a solid-state imaging device for which moisture resistance can be obtained and an endoscope using the same.

To attain the above object, in accordance with a first aspect of the invention, there is provided a solid-state imaging device comprising: a solid-state imaging element comprising a solid-state imaging element body; a first substrate one end face of which is bonded to and integrated with one end face of a solid-state imaging element substrate of the solid-state imaging element, the first substrate comprising on its one surface an electrode for establishing electrical contact with a bonding wire led from a pad provided on one surface of the solid-state imaging element, a frame that seals the solid-state imaging element so as to surround outer peripheral surfaces of the solid-state imaging element substrate excluding its the one end face; and a sealing resin portion that covers a region extending from a portion including the electrode on the surface of the first substrate to a portion including the pad on the one surface of the solid-state imaging element.

In accordance with the above-described first aspect of the invention, the solid-state imaging device can be made further compact and thinner in size. Also, the package of the solid-state imaging element can be formed with a size substantially equivalent to that of the solid-state imaging element, and moisture resistance can be ensured therefor.

In accordance with a second aspect of the invention, a gap is formed between the solid-state imaging element and the frame, and the gap is sealed with a moisture-resistant resin.

According to the above-described second aspect, since the gap is sealed with the moisture-resistant resin, moisture resistance is ensured. Therefore, even in cases where the solid-state imaging device is used in places where the humidity and the water content are high, there are no risks of electrical failures and short circuits, thereby making it possible to attain improvement of reliability.

In accordance with a third aspect of the invention, the resin is a thermosetting epoxy resin.

According to the above-described third aspect, since the sealed gap portion undergoes small volume shrinkage during curing, and the sealed gap portion excels in strength and toughness and has an extremely improved chemical resistance against solvents and the like after curing.

In accordance with a fourth aspect of the invention, the frame is formed by a metal plate.

In accordance with a fifth aspect of the invention, there is provided an electronic endoscope comprising the solid-state imaging device according to any one of the above-described first to fourth aspects provided in one of an interior of a distal end portion and a distal end side portion of the endoscope.

According to the above-described fifth aspect, in cases such as where the solid-state imaging device is used in an endoscope apparatus for observation of organisms, since moisture resistance is ensured, there are no risks of electrical failures and short circuits, thereby making it possible to attain improvement of safety and reliability.

DETAILED DESCRIPTION OF THE INVENTION

Referring now to the accompanying drawings, a detailed description will be given of the embodiments of the invention.

FIRST EMBODIMENT

Figure 1A:
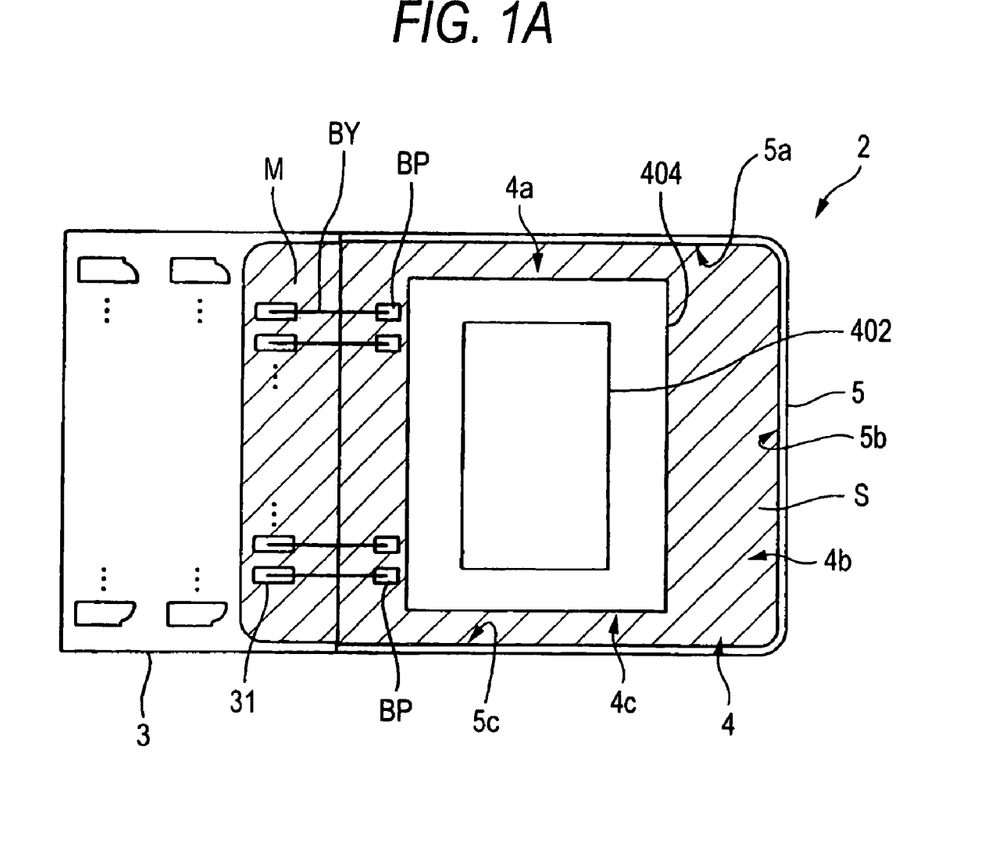
FIG. 1A is a plan view illustrating a solid-state imaging device in accordance with a first embodiment of the invention.
Figure 1B:
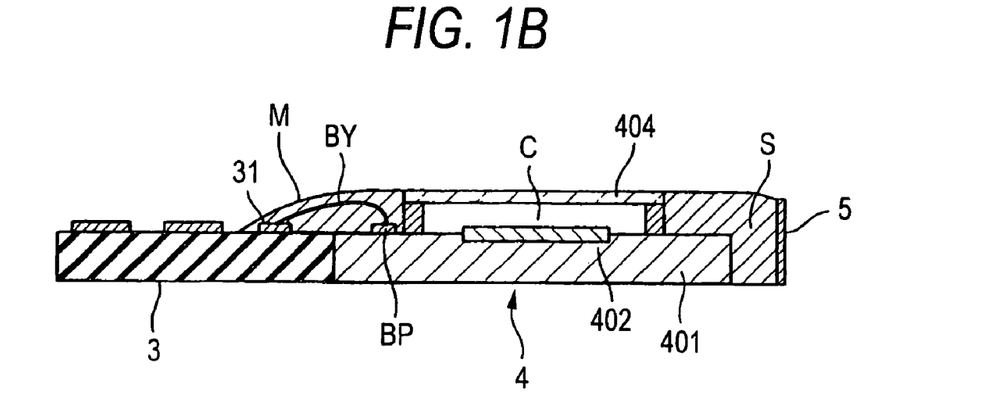
FIG. 1B is a cross-sectional view thereof.

As shown in FIGS. 1A and 1B, a solid-state imaging device 2 in accordance with a first embodiment has a substrate 3, a solid-state imaging element 4, and a frame 5. It should be noted that in the drawing reference character M denotes a sealing resin portion.

Of these members, the substrate 3 is formed of a ceramic and has a substantially plate-like shape, and one end face thereof (a right end face in FIG. 1B) is integrated with one end face (a left end face in FIG. 1B) of the solid-state imaging element 4 by being fixed with an appropriate adhesive, e.g., a UV adhesive.

Figure 2A:
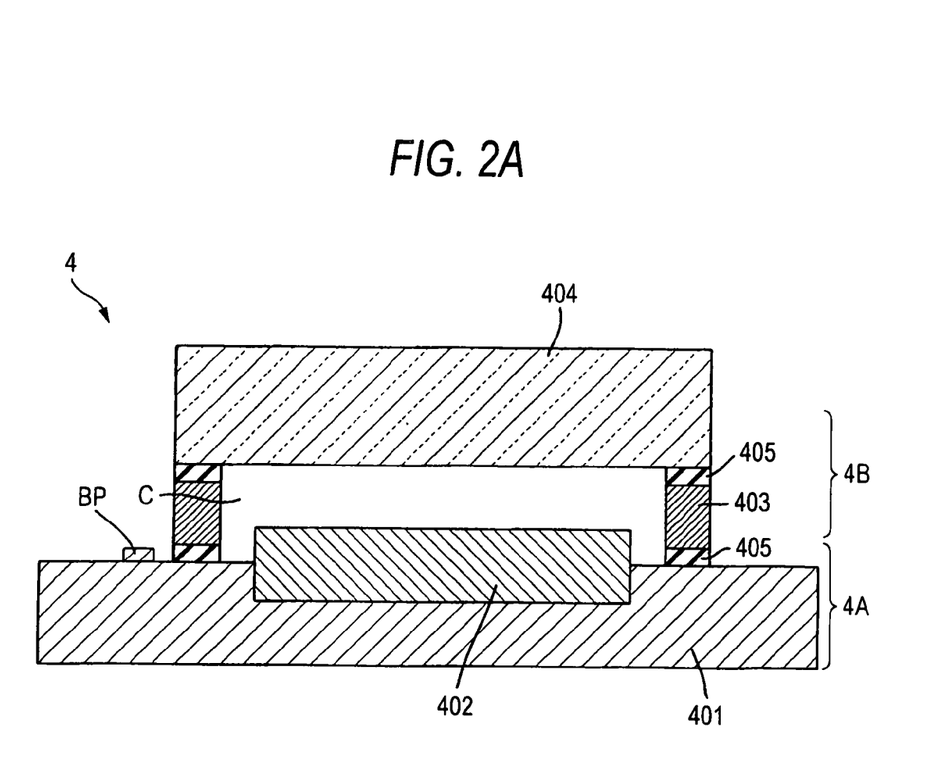
FIG. 2A is a cross-sectional view illustrating a schematic construction of a solid-state imaging element in accordance with the first embodiment.

The solid-state imaging element 4 is configured by a chip size package (CSP) type solid-state imaging element, and in terms of its general configuration the solid-state imaging element 4 has a solid-state imaging element substrate 4A and a cover glass 4B, as shown in FIG. 2A. Of these members, the solid-state imaging element substrate 4A has a silicon substrate 401 and a solid-state imaging element body (hereafter abbreviated as the main body portion) 402 constituted by a CCD formed on this silicon substrate. Further, bonding pads BP are formed on an upper surface of the silicon substrate 401, and these bonding pads BP and electrodes 31 provided on one surface (FIG. 1B) of the substrate 3 are electrically connected, as shown in FIGS. 1A and 1B. Furthermore, in FIGS. 1A and 1B, a region (connected by the bonding wires BY) extending from that portion on the upper surface side of the silicon substrate 401 where the bonding pads BP are provided to that portion on the upper surface side of the substrate 3 where the electrodes 31 are provided is covered with an appropriate insulating resin, e.g., a thermosetting epoxy resin, to thereby form the resin sealing portion M.

The frame 5 formed of a metal plate is arranged to surround through the resin sealing portion M outer peripheral surfaces, particularly three end faces (i.e., three outer peripheral surfaces indicated at reference numerals 4a to 4c in FIG. 1A) of the silicon substrate 401 constituting a part of the solid-state imaging element 4. The frame 5 in this embodiment is formed of stainless steel.

Figure 2B:
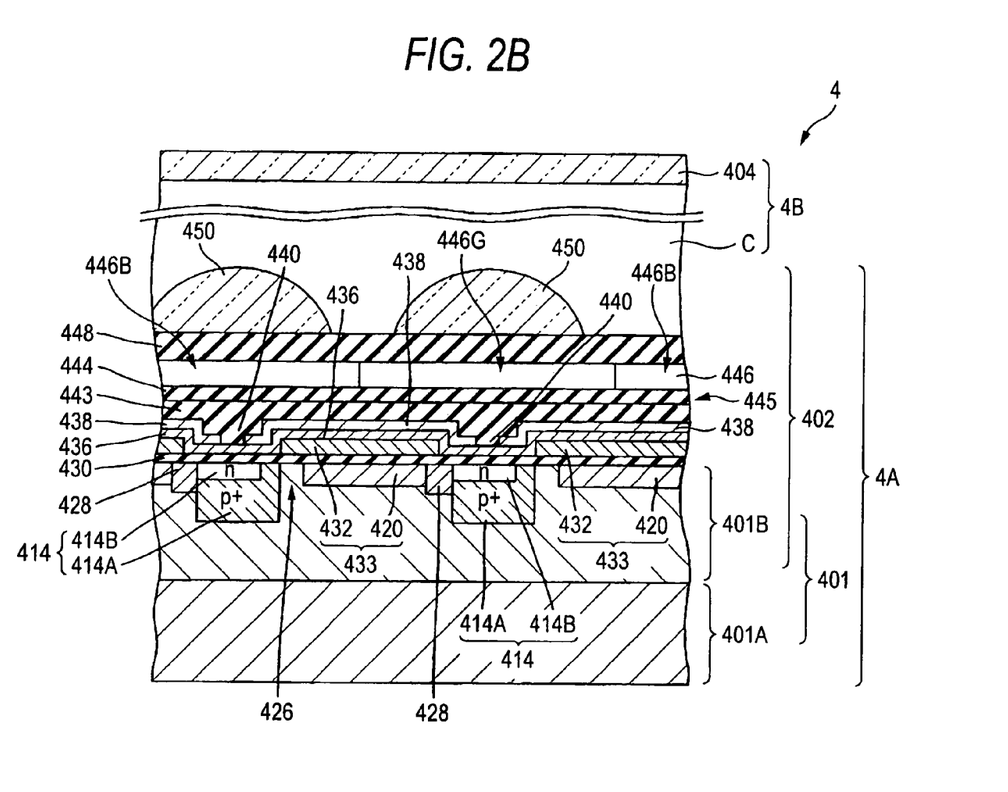
FIG. 2B is a cross-sectional view illustrating the construction of a solid-state imaging element substrate.

The cover glass 4B is mounted immediately above an incident surface (upper surface in FIGS. 1B and 2A), on which color filter layers 446R, 446G, and 446B (the color filter layer 446R, however, is not shown here in view of the positional relationship of the cutting plane) of the main body portion 402, microlenses 450, and the like are provided, as shown in FIG. 2B. Namely, this cover glass 4B includes a spacer 403 and a glass plate 404 serving as a translucent member bonded by appropriate adhesive layers 405 through this spacer 403, and is adapted to cover the incident surface of the main body portion 402. The spacer 403 in this embodiment is installed in such a manner as to surround the peripheries of the incident surface of the main body portion 402, and is adapted to form a gap C between the cover glass 4B and the incident surface of the main body portion 402 (silicon substrate 401). In addition, a nitrogen (N2) gas is sealed in the gap C of this embodiment, so as to prevent the color filter from being discolored due to contact with air, and prevent the color filter layers from exfoliating due to physical contact with the cover glass 4B.

Next, referring to FIGS. 2A and 2B, a detailed description will be given of the solid-state imaging element 4 in accordance with this embodiment.

As a cross-sectional view and an enlarged cross-sectional view of essential portions are respectively shown in FIGS. 2A and 2B, this solid-state imaging element 4 is constructed such that, as described before, the glass plate 404 is bonded to the surface of the silicon substrate 401 by means of the spacer 403 so as to form the gap C in correspondence with the light receiving area of the silicon substrate 401, and electrical contact with an external circuit (not shown) is established through the bonding pads BP formed on the surface of the silicon substrate 401 at its peripheral portions which have been discretely separated by dicing and are exposed from the glass plate 404. Here, the height of the spacer 403 is set to 10 to 500 μm, preferably 80 to 120 μm.

As shown in the enlarged cross-sectional view of essential portions in FIG. 2B, the solid-state imaging element substrate 4A is comprised of the silicon substrate 401 and the main body portion 402 arranged thereon, the R, G, and B color filter layers 446 and the microlenses 450 being formed on an upper surface thereof.

In this main body portion 402, a channel stopper 428 is formed in a p-well 401B formed on the surface of an n-type silicon substrate 401A, and a photodiode 414 and a charge transfer element 433 are formed with this channel stopper 428 interposed therebetween. Here, an n-type region 414B is formed in a p$^+$-type region 414A to thereby form the photodiode 414. In addition, a vertical charge transfer channel 420 constituted by an n-type region with a depth of 0.3 μm or thereabouts is formed in the p$^+$-type region 414A, and a vertical charge transfer electrode 432 constituted by a polycrystalline silicon layer formed via a gate insulating film 430 constituted by a silicon oxide film is formed on this upper layer, to thereby form a charge transfer element 433. In addition, a channel 426 for a reading gate formed by a p-type impurity region is formed between this vertical charge transfer channel 420 and the photodiode 414 on the side for reading a signal charge.

Meanwhile, the n-type impurity region 414B is exposed on the surface of the silicon substrate 401 along this channel 426 for a reading gate, and the signal charge generated in the photodiode 414 is temporarily accumulated in the n-type impurity region 414B, and is then read through the channel 426 for a reading gate.

The channel stopper 428 constituted by a p$^+$-type impurity region is present between the vertical charge transfer channel 420 and another photodiode 414. Consequently, the photodiode 414 and the vertical charge transfer channel 420 are electrically isolated from each other, and the vertical charge transfer channels 420 are also isolated so as not to come into contact with each other.

Further, the vertical charge transfer electrode 432 is formed such that it covers the channel 426 for a reading gate, while it exposes the n-type impurity region 414B and exposes a portion of the channel stopper 428 as well. A signal charge is transferred from the channel 426 for a reading gate which is located below any vertical charge transfer electrode 432 to which a reading signal is applied.

The vertical charge transfer electrode 432 constitutes, together with the vertical charge transfer channel 420, a vertical charge transfer device (VCCD) 433 for transferring in a vertical direction a signal charge generated by the pn junction of the photodiode 414. The surface of the substrate with the vertical charge transfer electrode 432 formed thereon is covered with a surface protective film 436, and a light shielding film 438 formed of tungsten is further provided on this upper layer. The arrangement provided is such that only a light receiving region 440 of the photodiode is open and other regions are shielded.

In addition, the upper layer of this vertical charge transfer electrode 432 is covered with a flattening insulating film 443 for surface flattening and a translucent resin film 444 formed on an upper layer thereof, and a filter layer 446 is further formed thereon. The filter layer 446 includes the red filter layer 446R (this red filter layer 446R, however, is not shown here in view of the positional relationship of the cutting plane), the green filter layer 446G, and the blue filter layer 446B which are arranged sequentially in order to form a predetermined pattern in correspondence with the respective photodiodes 414.

Moreover, this upper layer is covered with a microlens array comprising the microlens 450 which are formed with a flattening insulating film 448 interposed therebetween by patterning a translucent resin containing a photosensitive resin having a refractive index of 1.3 to 2.0 by an etching method using photolithography, and then by fusing the patterned translucent resin and rounding it by surface tension, followed by cooling.

Next, a description will be given of a process for manufacturing the solid-state imaging device 2 which is installed in an electronic endoscope in accordance with this embodiment. It should be noted that this method is based on a so-called wafer level CSP method in which positioning is carried out on a wafer level, collective mounting is performed for integration, and separation into each solid-state imaging device 4 is then executed, as manufacturing process diagrams are shown in FIGS. 3A to 6D. This method is characterized in that the sealing cover glass 4B with a spacer is used on which the spacer 403 is formed in advance.

Figure 3A:
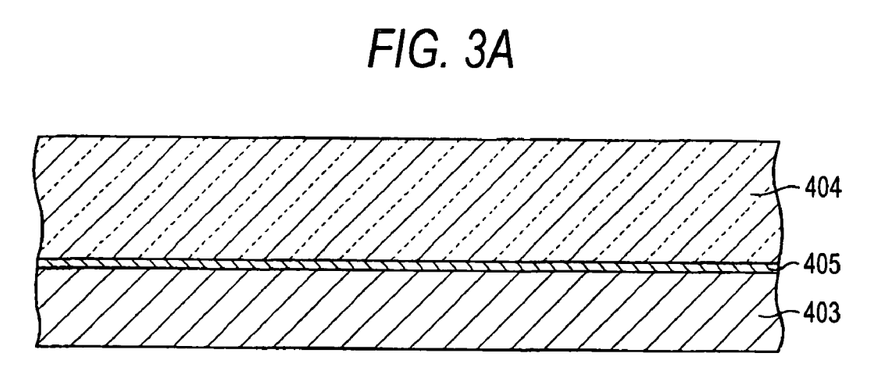
FIGS. 3A and 3B are explanatory diagrams illustrating parts of a method of manufacturing the solid-state imaging element in accordance with the first embodiment.

(1) First, as shown in FIG. 3A, the silicon substrate 403 serving as a spacer is bonded to the surface of the glass plate 404 through the adhesive layers 405 constituted by an ultraviolet curing type adhesive (e.g., a cationic polymerizable curing adhesive), and ultraviolet rays are applied from an unillustrated UV light source to cure the UV curing type adhesive. As a result, the glass plate 404 and the silicon substrate 403 are integrally fixed to each other.

Figure 3B:
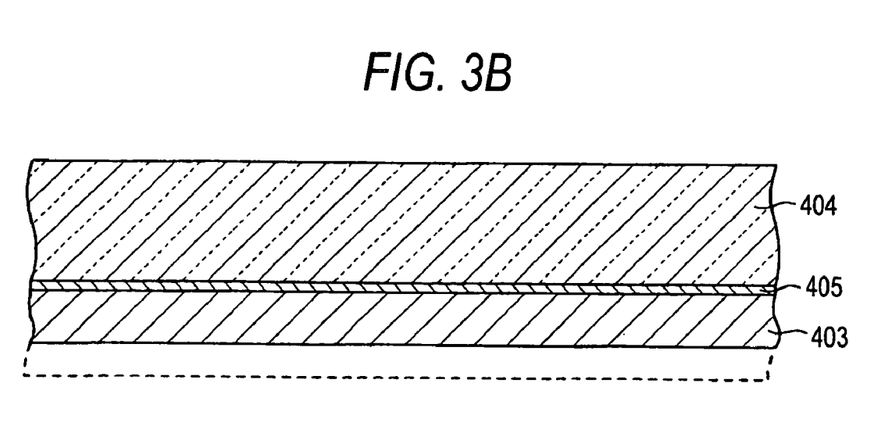

Next, as shown in FIG. 3B, the silicon substrate 403 is thinned down to a desired thickness and flattened by an appropriate means such as a known chemical mechanical polishing (CMP).

(2) Subsequently, as shown in FIGS. 4A to 4D, unnecessary portions of the silicon substrate 403 are etched off by an etching method using photolithography, while leaving a resist pattern at the portions of the silicon substrate 403 serving as the spacers, thereby forming the spacers.

Figure 4A:
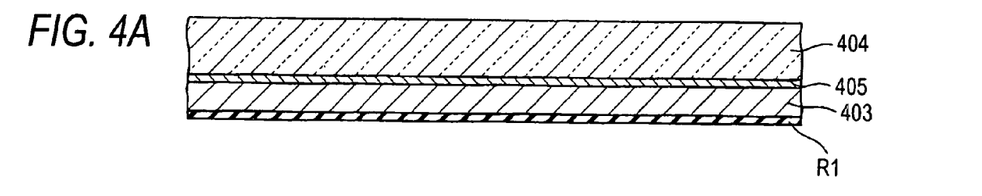
FIGS. 4A to 4D are explanatory diagrams illustrating parts of the method of manufacturing the solid-state imaging element in accordance with the first embodiment.
Figure 4B:
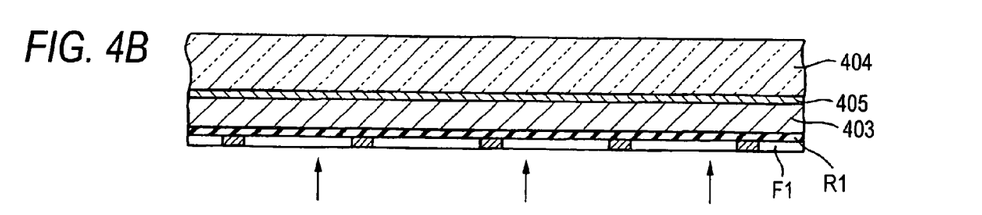
Figure 4C:
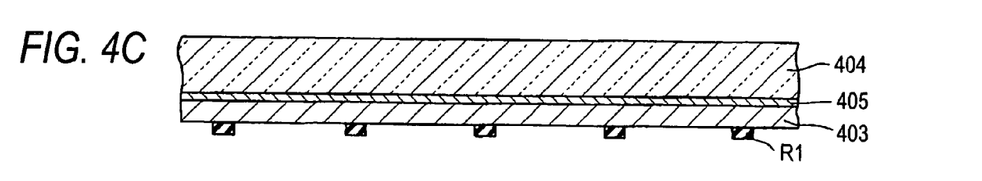
Figure 4D:
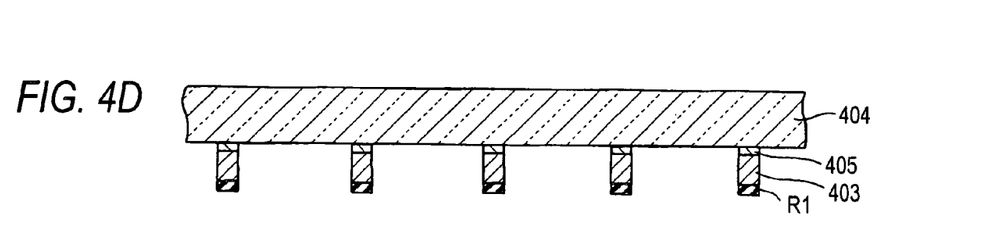

Namely, in this embodiment, a mask resist R1 is first applied to the entire surface of the silicon substrate 403, as shown in FIG. 4A. Next, exposure is carried out with a photo mask F1 (a positive type is used in this embodiment, but a negative type may, of course, be used) with a desired pattern formed thereon (FIG. 4B). Subsequently, development is performed to remove the mask resist R1 in regions excluding the portions corresponding to the necessary spacers (FIG. 4C). Then, dry etching is carried out to remove the silicon substrate 403 and the adhesive layers 405 excluding the regions where the mask resist R1 is coated (FIG. 4D).

Figure 5:
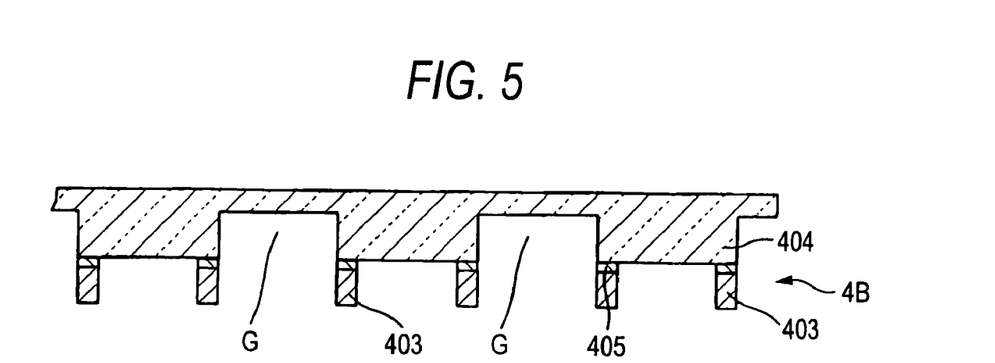
FIG. 5 is an explanatory diagram illustrating a part of the method of manufacturing the solid-state imaging element in accordance with the first embodiment.

(3) In addition, as shown in FIG. 5, grooving is carried out by using a slicer and a blade to form grooves G between devices.

Figure 6A:
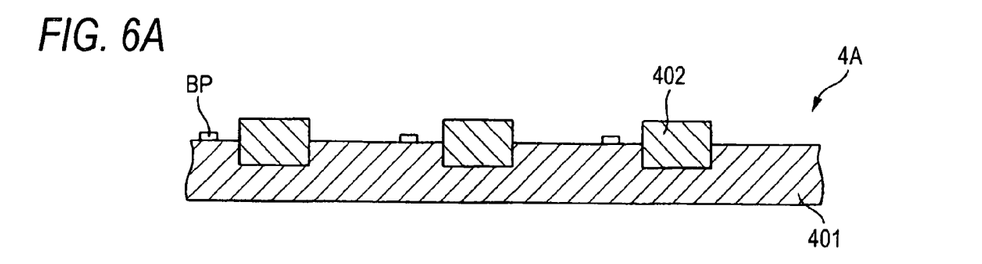
FIGS. 6A to 6D are explanatory diagrams illustrating parts of the method of manufacturing the solid-state imaging element in accordance with the first embodiment.

(4) Then, the solid-state imaging element substrate 4A is formed. In the formation of this solid-state imaging element substrate 4A, by preparing the silicon substrate 401 in advance, as shown in FIG. 6A, channel stopper layers are formed, channel regions are formed, and element regions for such as electric charge transfer electrodes are formed, although none of them are shown, by using an ordinary silicon process. Moreover, a wiring layer is formed on the surface, and the bonding pads BP constituted by a gold layer are formed for external connection.

Figure 6B:
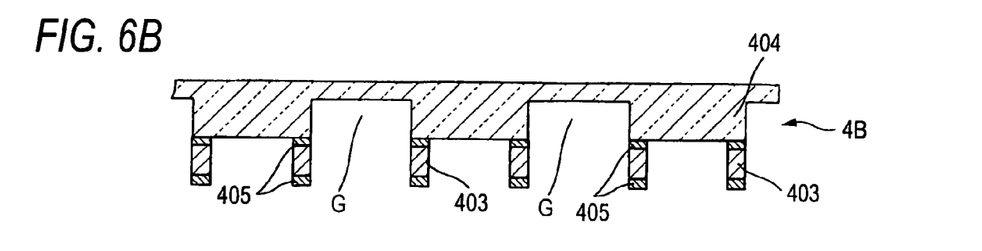
Figure 6C:
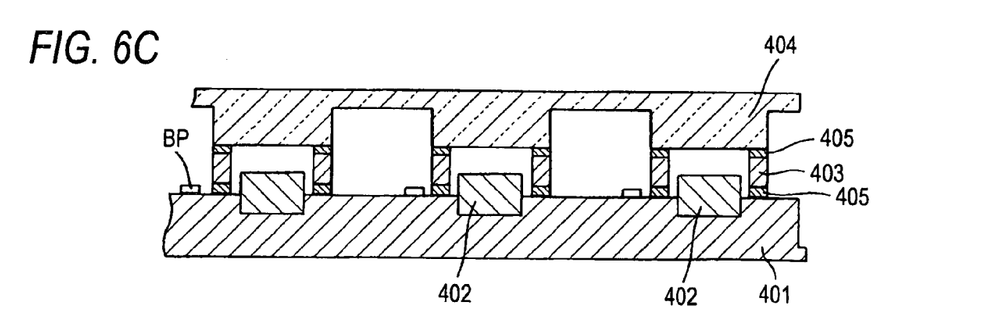

(5) Then, the solid-state imaging element substrate 4A shown in FIG. 6A and the cover glass 4B shown in FIG. 6B are joined and integrated to form a plurality of solid-state imaging elements 4. Namely, as shown in FIG. 6C, the positioning of the solid-state imaging element substrate 4A and the cover glass 4B is carried out by means of unillustrated cover marks formed on peripheral edges of the solid-state imaging element substrate 4A and the cover glass 4B. The sealing cover glass 4B is mounted on the solid-state imaging element substrate 4A with the element regions formed thereon in the above-described manner, and this assembly is subjected to heating to allow the two members to be integrated by means of the adhesive layers 405. It is desirable that this process should be executed in a vacuum or an inert gas atmosphere such as a nitrogen gas. In the integration, it is also possible to use not only a thermosetting adhesive but also a thermosetting and ultraviolet curing adhesive. In a case where the surface of the solid-state imaging element substrate 4A is formed of Si or metal, it is also possible to carry out bonding by surface activating cold bonding without using an adhesive.

Figure 6D:
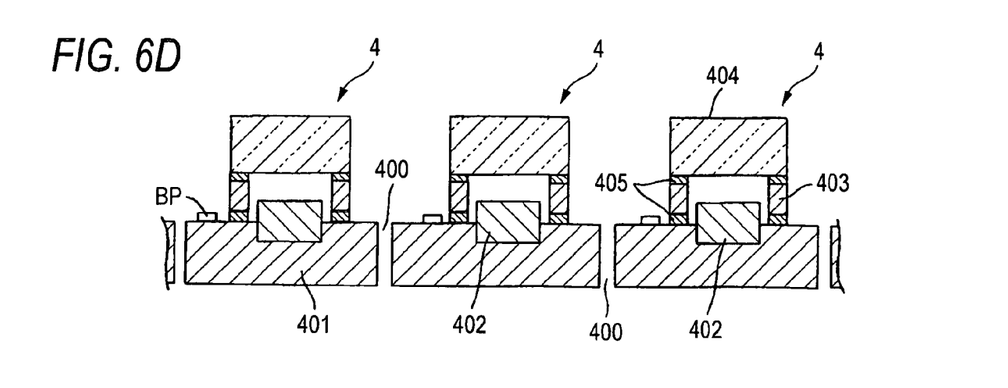

Furthermore, as shown in FIG. 6D, dicing is performed from the cover glass 4B (glass plate) side (upper surface in FIG. 6D) by using a blade, thereby separating the bonded assembly into individual solid-state imaging elements 4. In FIG. 6D, reference numeral 400 denotes a cut groove which is formed by dicing.

(6) Next, the solid-state imaging element 4 thus formed and the frame 5 prepared separately are joined to and integrated with the substrate 3, so that the solid-state imaging device 2 shown in FIGS. 1A and 1B is individually formed ultimately.

Figure 7:
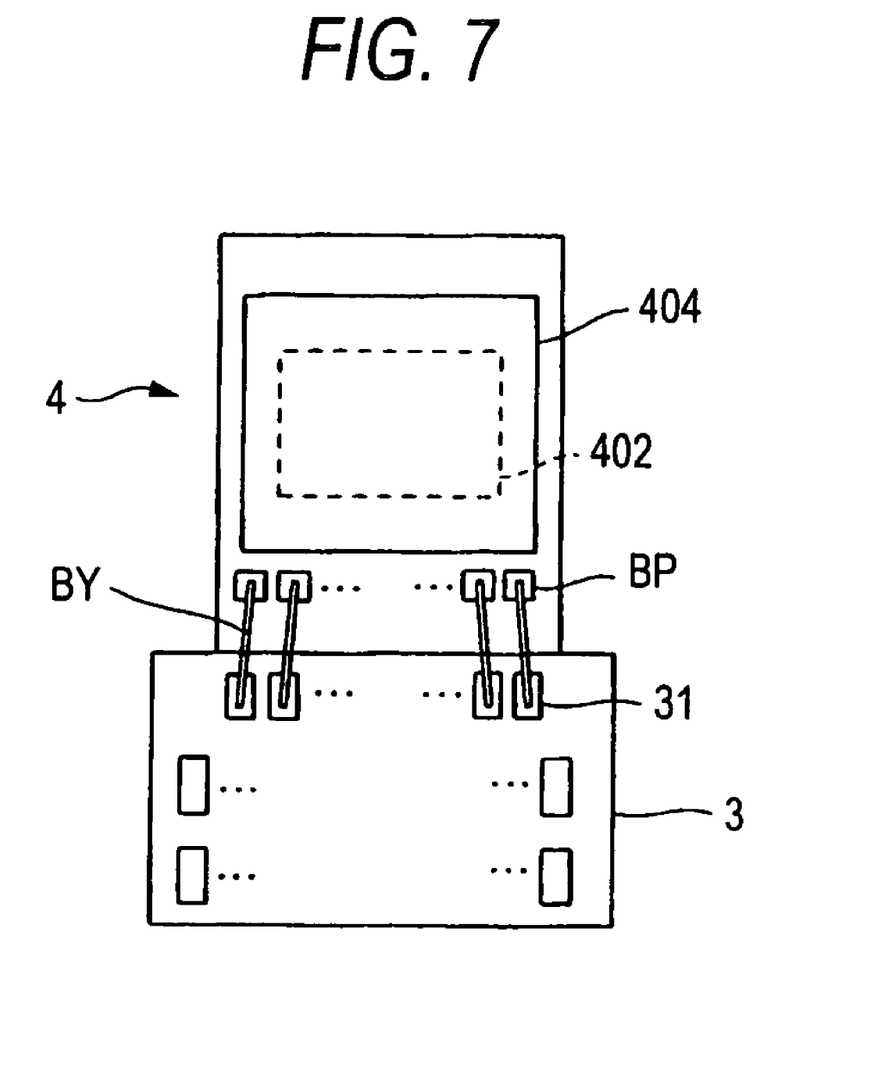
FIG. 7 is an explanatory diagram of a bonded state of a substrate and the solid-state imaging element, illustrating apart of the method of manufacturing the solid-state imaging element in accordance with the first embodiment.

Namely, first, the solid-state imaging element 4 and the substrate 3 shown in FIG. 7 are bonded to each other by using an appropriate adhesive such as an ultraviolet curing adhesive (e.g., a cationic polymerizable curing adhesive) and by applying ultraviolet rays from a UV light source. Then, the bonding pads BP on the solid-state imaging element 4 side and the electrodes 31 on the substrate 3 side are connected by the bonding wire BY such as a gold wire by using a wire bonder. Then, the regions including the bonding pads BP and the electrodes 31 on the substrate 3 side are covered with an insulating resin, e.g., a thermosetting epoxy resin, thereby forming the resin sealing portion M whereby an insulating property is ensured (see FIGS. 1A and 1B).

In this way, one end face portions on both sides of the substrate 3 having the solid-state imaging element 4 integrated therewith and both distal end faces of the aforementioned frame 5 having a substantially U-shape are brought into pressure contact with each other by using an appropriate adhesive. Also, by using, for example, an ultraviolet curing adhesive (e.g., a cationic polymerizable curing adhesive) in the same way as described above, ultraviolet rays are applied from a UV light source, thereby integrally fixing the integrated assembly by bonding, as shown in FIGS. 1A and 1B. In addition, since a gap S is formed between the solid-state imaging element 4 and the frame 5, this gap S is sealed by being filled with an appropriate resin, to thereby ensure moisture resistance and the like. Namely, as the resin for sealing the gap S between, on the one hand, outer peripheries (4a to 4c) of this solid-state imaging element 4 and, on the other hand, inner peripheries (5a to 5c) of the frame 5, as well as the space above the upper surface portion of the silicon substrate 401 around the cover glass 4B, the resin should preferably have such properties that its coefficients of thermal expansion and thermal shrinkage during curing are low to ensure that the solid-state imaging element 4 and the frame 5 will not be exfoliated from the substrate 3 due to a large expanding force or a large shrinking force particularly during curing. In this embodiment, the sealing is effected with a thermosetting epoxy resin or the like. The thermosetting epoxy resin used in this embodiment has a viscosity of 450 Pa·s, a glass transition temperature of 105° C., a modulus of elasticity of 25000 Mpa, and a curing condition of 100° C. 1 Hr/150° C. 3 Hrs. It should be noted that in a case where the gap S between the frame 5 and the solid-state imaging element 4 is sealed with a resin which is supplied from an unillustrated dispenser, if the integrated assembly is placed on an unillustrated flat susceptor, and the aforementioned resin is used to fill the gap S, the resin flows into the gap S between the frame 5 and the solid-state imaging element 4, thereby firmly fixing the gap S by the resin. In this case, although it depends on the environment and atmosphere of the place where the manufacturing apparatus of the solid-state imaging devices is installed, if a resin is used which has appropriate properties including such a viscosity that the resin is expected to cure in a state in which its surface has become high to some extent due to surface tension, it is possible to prevent such as a situation in which as the resin flows downward due to its own weight, the resin flows round beneath the solid-state imaging element substrate 4A, and fixes even the susceptor.

Therefore, according to this embodiment, as shown in FIGS. 2A and 2B, unlike the related-art solid-state imaging element, the solid-state imaging element 4 is not so constructed as to be mounted on the package body, but is constituted by only the solid-state imaging element substrate 4A and the cover glass 4B. Therefore, as compared with the related-art solid-state imaging device, it becomes possible to make the solid-state imaging device thin by the thickness of the package body portion which is unrequired.

In addition, according to this embodiment, the gap S between the solid-state imaging element 4 and its surrounding frame 5 is sealed with the moisture-resistant sealing resin portion M, so that moisture resistance is ensured for the solid-state imaging element 4. Therefore, even in cases where the solid-state imaging device is used in places where the humidity and the water content are high, there are no risks of electrical failures and short circuits, and it is possible to realize a highly reliable solid-state imaging device. Moreover, in this embodiment, since a thermosetting epoxy resin, in particular, is used as the resin for sealing the gap S between the solid-state imaging element 4 and its surrounding frame 5, the sealed gap portion undergoes small volume shrinkage during curing, and various properties can be obtained in that the sealed gap portion excels in strength and toughness and has an extremely excellent chemical resistance against solvents and the like after curing.

Although in this embodiment the wiring layer including the bonding pads BP is formed of a metal layer, the wiring layer is not limited to the metal layer, and it goes without saying that aluminum or other metal, or another conductor layer such as silicides, may be used. In addition, the microlens array can alternatively be formed by forming a translucent resin film on the substrate surface in advance and forming a lens layer having a refractive index gradient at a predetermined depth by ion implantation from this surface. Furthermore, as the spacer, it is possible to appropriately select from among such as a 42-alloy, a metal, a glass, a photosensitive polyimide, and a polycarbonate resin in addition to the silicon substrate.

SECOND EMBODIMENT

Figure 8:
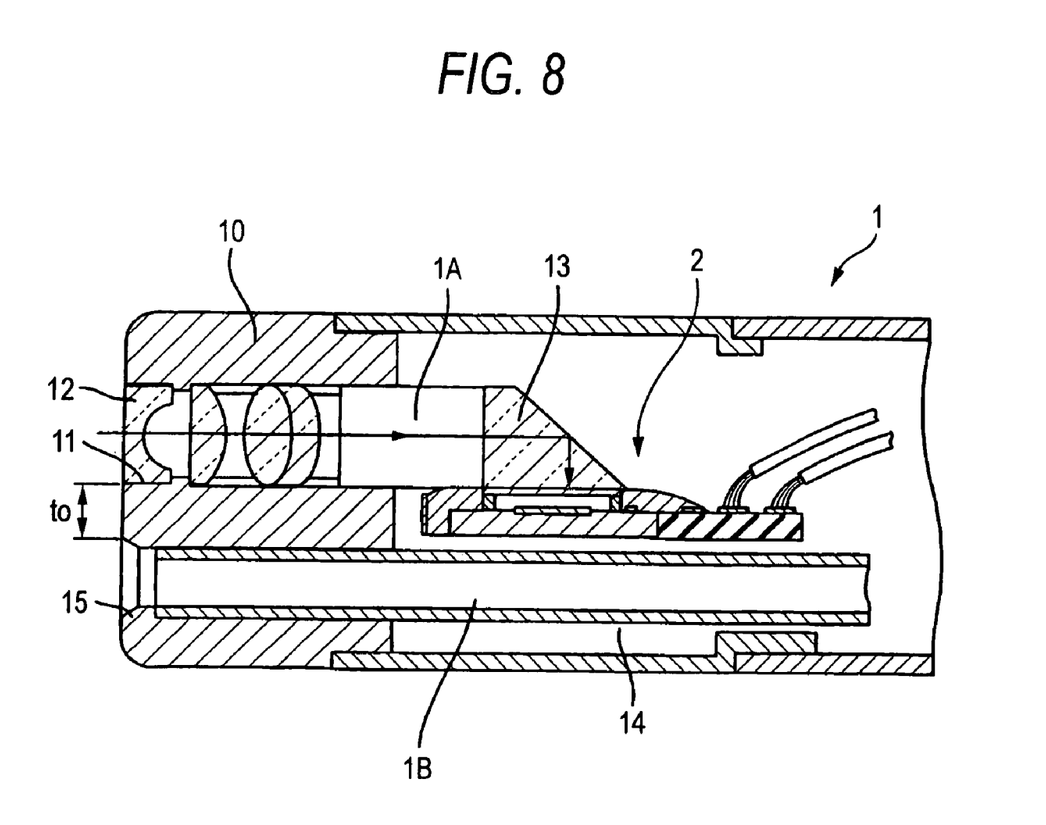
FIG. 8 is a cross-sectional view of essential portions illustrating a distal end portion of an electronic endoscope in accordance with a second embodiment of the invention.

FIG. 8 shows a direct-viewing type electronic endoscope provided with the solid-state imaging device in accordance with a second embodiment of the invention. In this electronic endoscope, the solid-state imaging device 2 in accordance with the first embodiment is installed in the interior of a distal end portion 10 of an endoscope body 1.

The endoscope body 1 is provided with an observation channel 1A for observing a region to be observed from an observation window 11, which is open at a distal end face, through an objective lens 12, a prism 13, and the like, as well as a treatment instrument insertion channel 1B for performing various treatments from a forceps window 15, which is open at the distal end face, by inserting an unillustrated treatment instrument through a forceps hole 14.

Therefore, according to this embodiment, as compared with the solid-state imaging device having the related-art thickness shown in FIG. 9, the solid-state imaging device 2 can be made compact, and particularly its thickness t0 (t0<t1 where t1 is the related-art thickness) can be made thin. Hence, the outside diameter of the distal end portion of the endoscope body 1 can be reduced by that portion, which in turn makes it possible to make the diameter of the endoscope small. In consequence, a narrow-diameter endoscope becomes possible, and when the interior of a living body is observed, insertion into a narrower organ becomes possible, so that many advantages can be expected clinically as well.

In addition, according to this embodiment, since it is possible to obtain water resistance at the electrical connecting portion between the solid-state imaging element 4 and the substrate 3 as well as moisture resistance of the solid-state imaging element 4, in cases such as where the solid-state imaging device is used in an endoscope apparatus for observation of organisms, there are no risks of electrical failures and short circuits, thereby making it possible to improve reliability.

It should be noted that although in this embodiment the solid-state imaging device 2 is configured to be applied to a direct-viewing type endoscope, it goes without saying that the solid-state imaging device 2 is also applicable to a side-viewing type endoscope.

It should be noted that the invention is not limited to the foregoing embodiments, and can be implemented in various forms within the scope that does not depart from its gist.

According to the invention, it is possible to realize a solid-state imaging device which can be made further compact and thinner in size, whose overall size including the package of the solid-state imaging element is made substantially the same size as the solid-state imaging element, and which is provided with moisture resistance, as well as an electronic endoscope having the solid-state imaging device.

The solid-state imaging device in accordance with the invention offers advantages in that the solid-state imaging device can be made further compact and thinner in size, and that the package of the solid-state imaging element can be formed with a size substantially equivalent to that of the solid-state imaging element, and moisture resistance can be ensured therefor. As this solid-state imaging device is mounted, a smaller-diameter body can be realized, and a nasal endoscope or the like hence becomes realizable. As such, the solid-state imaging device in accordance with the invention is useful for an electronic endoscope and the like.

The entire disclosure of each and every foreign patent application from which the benefit of foreign priority has been claimed in the present application is incorporated herein by reference, as if fully set forth.

What is claimed is:

1. A solid-state imaging device comprising:
   a solid-state imaging element comprising a solid-state imaging element body;
   a first substrate one end face of which is bonded to and integrated with one end face of a solid-state imaging element substrate of the solid-state imaging element, the first substrate comprising on its one surface an electrode for establishing electrical contact with a bonding wire led from a pad provided on one surface of the solid-state imaging element,
   a frame that seals the solid-state imaging element so as to surround outer peripheral surfaces of the solid-state imaging element substrate excluding its the one end face; and
   a sealing resin portion that covers a region extending from a portion including the electrode on the one surface of the first substrate to a portion including the pad on the one surface of the solid-state imaging element.

2. The solid-state imaging device according to claim 1, wherein a gap is formed between the solid-state imaging element and the frame, and
   the gap is sealed with a moisture-resistant resin.

3. The solid-state imaging device according to claim 2, wherein the resin is a thermosetting epoxy resin.

4. The solid-state imaging device according to claim 1, wherein the frame is formed by a metal plate.

5. An electronic endoscope comprising the solid-state imaging device according to claim 1 provided in one of an interior of a distal end portion and a distal end side portion of the endoscope.

6. A solid-state imaging device comprising:
   a first substrate having a top face and a plurality of side faces;
   an imaging element body on top of the first substrate;
   a second substrate having a top face and a plurality of side faces;
   wherein one of the plurality of side faces of the second substrate abuts one of the plurality of faces of the first substrate;
   wherein the top face of the second substrate has an electrode for establishing electrical contact with a bonding wire led from a pad provided on the top face of the first substrate;
   wherein the solid-state imaging device further comprises a frame that surrounds the plurality of side faces of the first substrate that do not abut the one of the plurality of faces of the second substrate; and
   a sealing resin that covers a portion of the top faces of the first and second substrates that contain the electrode and pad, respectively.

7. The solid-state imaging device according to claim 6, wherein a gap is formed between the plurality of side faces of the first substrate and the frame, and wherein the sealing resin fills the gap, thereby insulating the first substrate and the imaging element body.

8. The solid-state imaging device according to claim 6, wherein the first substrate is made of silicon and the second substrate is made of ceramic.

9. The solid-state imaging device according to claim 6, wherein the frame is made of stainless steel.

10. The solid-state imaging device according to claim 6, wherein a glass plate is bonded to the surface of the first substrate by means of a spacer so as to form a gap above the imaging element body on top of the first substrate.

11. The solid-state imaging device according to claim 10, wherein the sealing resin further covers side portions of the glass plate and the spacer, thereby sealing the gap so that moisture resistance is ensured for the imaging element body.

12. The solid-state imaging device according to claim 6, wherein the first substrate and the second substrate form a common plane.

* * * * *